US00PP22686P2

(12) United States Plant Patent
Elliot

(10) Patent No.: US PP22,686 P2
(45) Date of Patent: Apr. 24, 2012

(54) ***BRACHYSCOME* PLANT NAMED 'CHERISH'**

(50) Latin Name: *Brachyscome angustifolia*
Varietal Denomination: Cherish

(75) Inventor: Rodger Elliot, Heathmont (AU)

(73) Assignee: Outback Plants Pty. Ltd., Cranbourne, Victoria (AU)

( * ) Notice: Subject to any disclaimer, the term of this patent is extended or adjusted under 35 U.S.C. 154(b) by 0 days.

(21) Appl. No.: 13/136,891

(22) Filed: Aug. 12, 2011

(51) Int. Cl.
*A01H 5/00* (2006.01)

(52) U.S. Cl. ..... Plt./411

(58) Field of Classification Search ..... Plt./411
See application file for complete search history.

*Primary Examiner* — June Hwu
*Assistant Examiner* — Louanne Krawczewicz Myers
(74) *Attorney, Agent, or Firm* — C. A. Whealy

(57) ABSTRACT

A new and distinct cultivar of *Brachyscome* plant named 'Cherish', characterized by its compact, low spreading and mounding plant habit; freely branching growth habit; durable dark green-colored leaves; freely flowering habit; large inflorescences positioned above the foliage; broad and bright red purple-colored ray florets; and good postproduction longevity.

2 Drawing Sheets

Botanical designation: *Brachyscome angustifolia.*
Cultivar denomination: 'CHERISH'.

BACKGROUND OF THE INVENTION

The present invention relates to a new and distinct cultivar of *Brachyscome* plant, botanically known as *Brachyscome angustifolia* and hereinafter referred to by the name 'Cherish'.

The new *Brachyscome* plant is a product of a controlled breeding program conducted by the Inventor in Cranbourne, Victoria, Australia. The objective of the breeding program is to create new compact *Brachyscome* plants with numerous large inflorescences and strong durable foliage.

The new *Brachyscome* plant originated from a cross-pollination conducted by the Inventor in Cranbourne, Victoria, Australia, of a proprietary selection of *Brachyscome angustifolia* identified as code name OB05506, not patented, as the female, or seed, parent with a proprietary selection of *Brachyscome angustifolia* identified as code name OB04547, not patented, as the male, or pollen, parent. The new *Brachyscome* plant was discovered and selected by the Inventor in August, 2007 as a single flowering plant from within the progeny of the stated cross-pollination in a controlled environment in Cranbourne, Victoria, Australia.

Asexual reproduction of the new *Brachyscome* plant by stem cuttings in a controlled environment in Cranbourne, Victoria, Australia since December, 2007 has shown that the unique features of this new *Brachyscome* plant are stable and reproduced true to type in successive generations.

SUMMARY OF THE INVENTION

Plants of the new *Brachyscome* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Cherish'.

These characteristics in combination distinguish 'Cherish' as a new and distinct *Brachyscome* plant:

1. Compact, low spreading and mounding plant habit.
2. Freely branching growth habit.
3. Durable dark green-colored leaves.
4. Freely flowering habit.
5. Large inflorescences positioned above the foliage.
6. Broad and bright red purple-colored ray florets.
7. Good postproduction longevity.

Plants of the new *Brachyscome* differ from plants of the female parent selection in the following characteristics:

1. Plants of the new *Brachyscome* are not as vigorous as plants of the female parent selection.
2. Plants of the new *Brachyscome* are more mounding than plants of the female parent selection.
3. Plants of the new *Brachyscome* and the female parent selection differ in ray floret color as plants of the female parent selection have slightly darker red purple-colored ray florets.

Plants of the new *Brachyscome* differ from plants of the male parent selection in the following characteristics:

1. Plants of the new *Brachyscome* are more vigorous than plants of the male parent selection.
2. Plants of the new *Brachyscome* are taller than plants of the male parent selection.
3. Plants of the new *Brachyscome* have larger inflorescences than plants of the male parent selection.
4. Plants of the new *Brachyscome* and the male parent selection differ in ray floret color as plants of the male parent selection have darker red purple-colored ray florets.

Plants of the new *Brachyscome* can also be compared to plants of the *Brachyscome angustifolia* 'Magenta Magic', disclosed in U.S. Plant Pat. No. 22,225. In side-by-side comparisons conducted in Cranbourne, Victoria, Australia, plants of the new *Brachyscome* differed from plants of 'Magenta Magic' in the following characteristics:

1. Plants of the new *Brachyscome* had shorter lateral branches and internodes than plants of 'Magenta Magic'.

2. Leaves of plants of the new *Brachyscome* and 'Magenta Magic' differed in leaf shape.
3. Plants of the new *Brachyscome* and 'Magenta Magic' differed in ray floret color as plants of 'Magenta Magic' had bright purple-colored ray florets.

BRIEF DESCRIPTION OF THE PHOTOGRAPHS

The accompanying colored photographs illustrate the overall appearance of the new *Brachyscome* plant showing the colors as true as it is reasonably possible to obtain in colored reproductions of this type. Colors in the photographs may differ slightly from the color values cited in the detailed botanical description which accurately describe the colors of the new *Brachyscome* plant.

The photograph on the first sheet comprises a top perspective view of a typical flowering plant of 'Cherish' grown in a container.

The photograph on the second sheet is a close-up view of typical inflorescences of 'Cherish'.

DETAILED BOTANICAL DESCRIPTION

The aforementioned photographs and following observations, measurements and values describe plants grown during the fall and winter in 15-cm containers in a polyethylene-covered greenhouse in Cranbourne, Victoria, Australia and under commercial practice with day temperatures ranging from 12° C. to 30° C., night temperatures ranging from 4° C. to 20° C. and light levels ranging from 5,000 lux to 9,000 foot candles. Plants were pinched twice and were six months old when the description was taken and one year old when the photographs were taken. In the following description, color references are made to The Royal Horticultural Society Colour Chart, 1995 Edition, except where general terms of ordinary dictionary significance are used.

Botanical classification: *Brachyscome angustifolia* 'Cherish'.

Parentage:

*Female, or seed, parent.*—Proprietary selection of *Brachyscome angustifolia* identified as code name OB05506, not patented.

*Male, or pollen, parent.*—Proprietary selection of *Brachyscome angustifolia* identified as code name OB04547, not patented.

Propagation:

*Type.*—By stem cuttings.

*Time to initiate roots, summer.*—About 13 to 23 days at temperatures of 22° C. to 30° C.

*Time to initiate roots, winter.*—About 18 to 31 days at temperatures of 15° C. to 22° C.

*Time to produce a rooted young plant, summer.*—About 20 to 30 days at temperatures of 16° C. to 39° C.

*Time to produce a rooted young plant, winter.*—About 25 to 45 days at temperatures of 10° C. to 20° C.

*Root description.*—Thin, fibrous; white in color.

*Rooting habit.*—Moderately freely branching; moderately dense.

Plant description:

*Plant form and growth habit.*—Compact, low spreading and mounded plant habit; moderately vigorous growth habit; freely branching habit with numerous lateral branches developing after pinching.

*Plant height.*—About 15 cm to 25 cm.

*Plant width (spread).*—About 25 cm to 60 cm.

*Lateral branches.*—Length: About 5 cm to 8 cm. Diameter: About 1 mm to 2 mm. Internode length: About 4 mm to 13 mm. Strength: Moderately strong; brittle when bent. Texture: Smooth, glabrous; occasionally, sparsely bristled. Color: When developing, close to 59A to 59B; with development, close to 137A to 137B.

Foliage description:

*Arrangement.*—Alternate, simple; sessile.

*Length.*—About 2.8 cm to 7.1 cm.

*Width.*—About 8 mm to 26 mm.

*Shape.*—Flaring into two or three lobes.

*Apex.*—Acute.

*Base.*—Amplexicaul.

*Margin.*—Entire; slightly undulate to flat; slightly recurved.

*Texture, upper and lower surfaces.*—Smooth, glabrous.

*Venation pattern.*—Pinnate.

*Color.*—Developing leaves, upper surface: Close to 137A. Developing leaves, lower surface: Close to 137C. Fully expanded leaves, upper surface: Close to 139A; venation, close to 139A. Fully expanded leaves, lower surface: Close to 137C; venation, close to 137A.

Inflorescence description:

*Inflorescence appearance and flowering habit.*—Single-type composite inflorescences with ray and disc florets; inflorescences terminal and borne above the foliar plane; freely flowering habit with numerous inflorescences developing per plant during the flowering period.

*Fragrance.*—None detected.

*Natural flowering season.*—Plants begin flowering about four to eight weeks after planting and flower continuously from spring through autumn in Australia.

*Inflorescence longevity.*—Inflorescences last about two to four weeks on the plant; inflorescences not persistent.

*Inflorescence bud.*—Height: About 2 mm to 3 mm. Diameter: About 3 mm. Shape: Oblate. Color: Close to 137D occasionally tinged with close to 59A.

*Inflorescence size.*—Height: About 7 mm to 9 mm. Diameter: About 2.8 cm to 3 cm. Diameter of disc: About 6 mm to 9 mm. Receptacle height: About 2 mm. Receptacle diameter: About 3 mm to 5 mm.

*Ray florets.*—Quantity and arrangement: About 13 to 23 in two whorls. Length: About 9 mm to 13 mm. Width: About 2 mm to 3 mm. Shape: Narrowly obovate. Apex: Bluntly acute or slightly emarginate. Base: Attenuate. Margin: Entire. Texture, upper and lower surfaces: Smooth, glabrous. Color: When opening, upper and lower surfaces: Close to 64A. Fully opened, upper surface: Close to 74A; color becoming closer to 78A with development. Fully opened, lower surface: Close to 74C; color becoming closer to 74D with development.

*Disc florets.*—Arrangement: About 50 massed at center of receptacle. Length: About 4 mm. Width: About 1 mm. Shape: Tubular, elongated. Apex: Five-pointed. Texture: Smooth, glabrous; satiny. Color, immature: Close to 151A. Color, mature: Close to 9A.

*Involucral bracts.*—Quantity and arrangement: About 18 to 24 arranged in a single whorl; bracts imbricate. Length: About 2 mm. Width: Less than 1 mm. Shape:

Oblong; keeled and concave. Apex: Bluntly acute or emarginate. Margin: Entire. Texture, upper surface: Slightly glandular and sparsely bristled. Texture, lower surface: Smooth, glabrous. Color, upper and lower surfaces: Close to 137B.

*Peduncles.*—Length: About 5.2 cm to 8.7 cm. Diameter: About 1 mm. Strength: Moderately strong. Texture: Smooth, glabrous. Color: Close to 137A to 137B.

*Reproductive organs.*—Present on disc florets only. Androecium: Filament length: About 2 mm. Filament color: Close to 155D. Anther length: Less than 1 mm. Anther shape: Oblong to lanceolate. Anther color: Close to 163C and 167D. Pollen amount: Scarce and yellowish. Gynoecium: Stigma shape: Bi-lobed. Style length: About 2 mm. Style color: Close to 155D.

*Seeds.*—Seed set is nil to scarce on plants of the new *Brachyscome.* Quantity per inflorescence: None to about three. Length: Less than 1 mm. Diameter: Less than 1 mm.

Disease & pest resistance: Plants of the new *Brachyscome* have not been observed to be resistant to pathogens and pests common to *Brachyscome* plants.

Garden performance: Plants of the new *Brachyscome* have been observed to have good garden performance and tolerate rain, wind and temperatures ranging from about −3° C. to about 47° C.

It is claimed:

1. A new and distinct *Brachyscome* plant named 'Cherish' as illustrated and described.

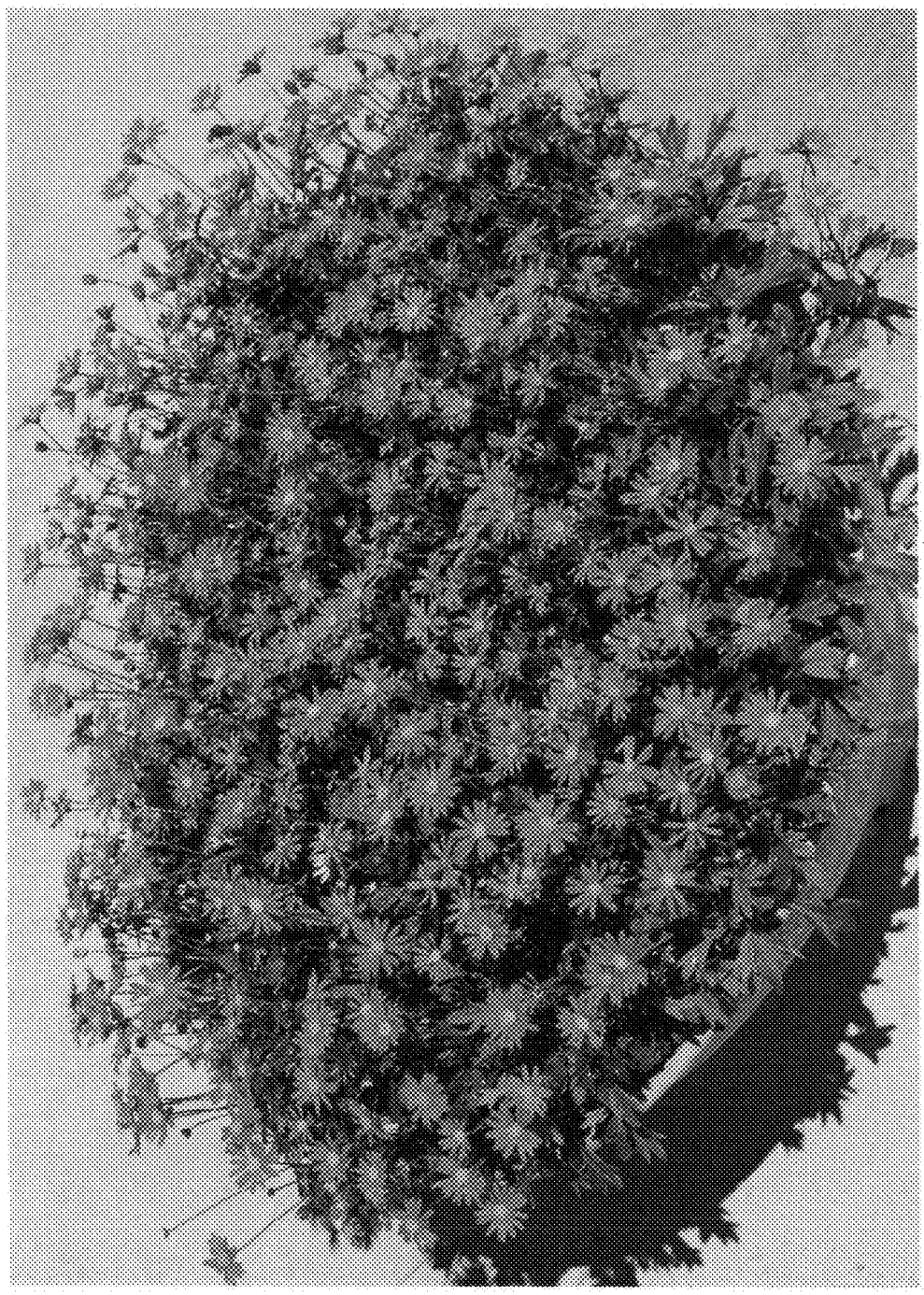

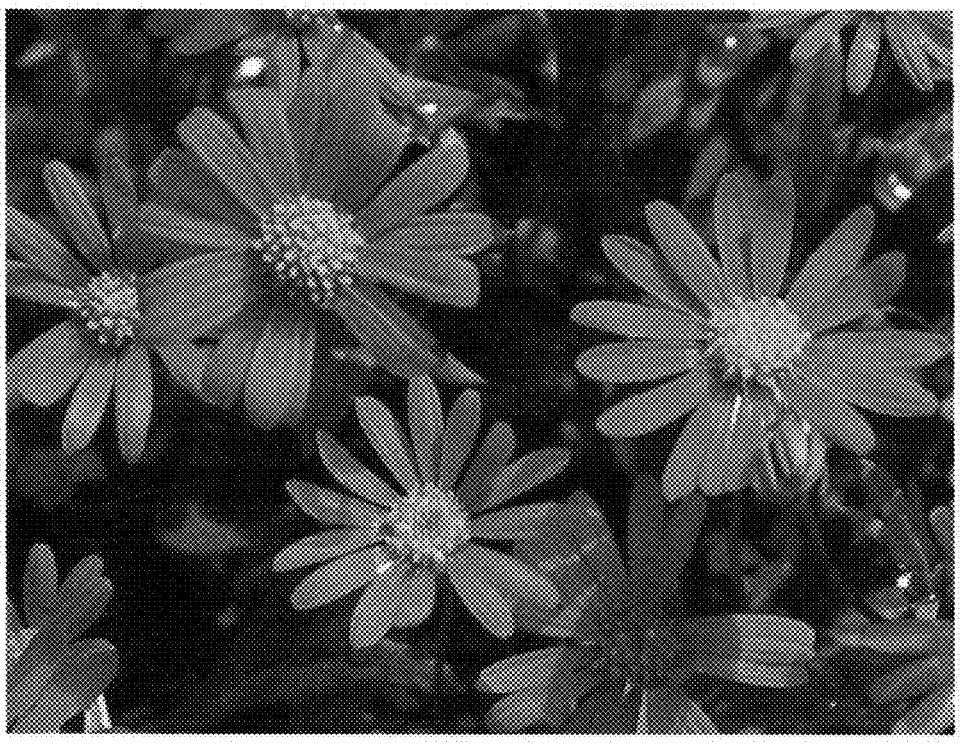

* * * * *